(12) United States Patent
Ge et al.

(10) Patent No.: US 8,241,678 B2
(45) Date of Patent: Aug. 14, 2012

(54) SYNERGISTIC ANTIOXIDANT COMBINATIONS OF HERB EXTRACTS AND METHODS RELATING THERETO

(75) Inventors: Haiyan Ge, Scottsdale, AZ (US); Earl P. Seitz, Scottsdale, AZ (US); Thomas Doering, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 12/977,352

(22) Filed: Dec. 23, 2010

(65) Prior Publication Data
US 2011/0135765 A1 Jun. 9, 2011

Related U.S. Application Data

(62) Division of application No. 12/342,483, filed on Dec. 23, 2008, now Pat. No. 7,897,183.

(51) Int. Cl.
*A61K 36/00* (2006.01)
*A61K 36/488* (2006.01)

(52) U.S. Cl. ........................................ 424/725; 424/757
(58) Field of Classification Search .................... None
See application file for complete search history.

(56) References Cited

FOREIGN PATENT DOCUMENTS
CN 101292947 A * 10/2008
JP 07215886 A * 8/1995

OTHER PUBLICATIONS

Yang et al, Investigation on the relativity between flavonoid content and antioxidant activation for eleven kinds of Chinese herbal medicine, Shipin Gongye Keji (2008), 29(1), 119-120, 123.*

* cited by examiner

*Primary Examiner* — Qiuwen Mi
(74) *Attorney, Agent, or Firm* — David K. Benson

(57) ABSTRACT

The present invention comprises mixtures of herb extracts which exert synergistic antioxidant effect and comprise the herb licorice and at least one other herb selected from the group consisting of ginger, kudzu, sophora, and thyme. Skin care preparations incorporating such herb extract mixtures, and their methods of preparation and use, are also claimed.

6 Claims, 5 Drawing Sheets

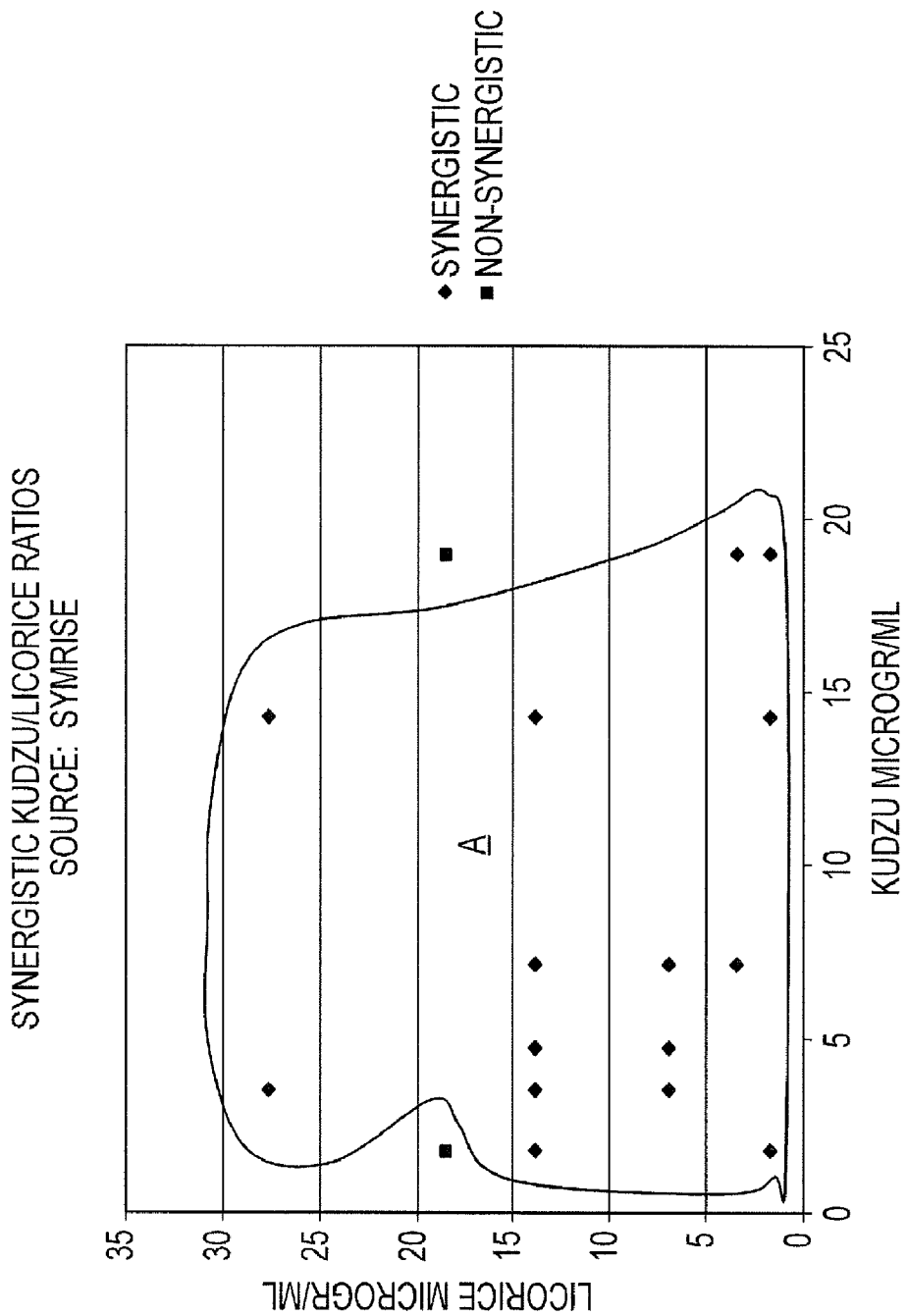

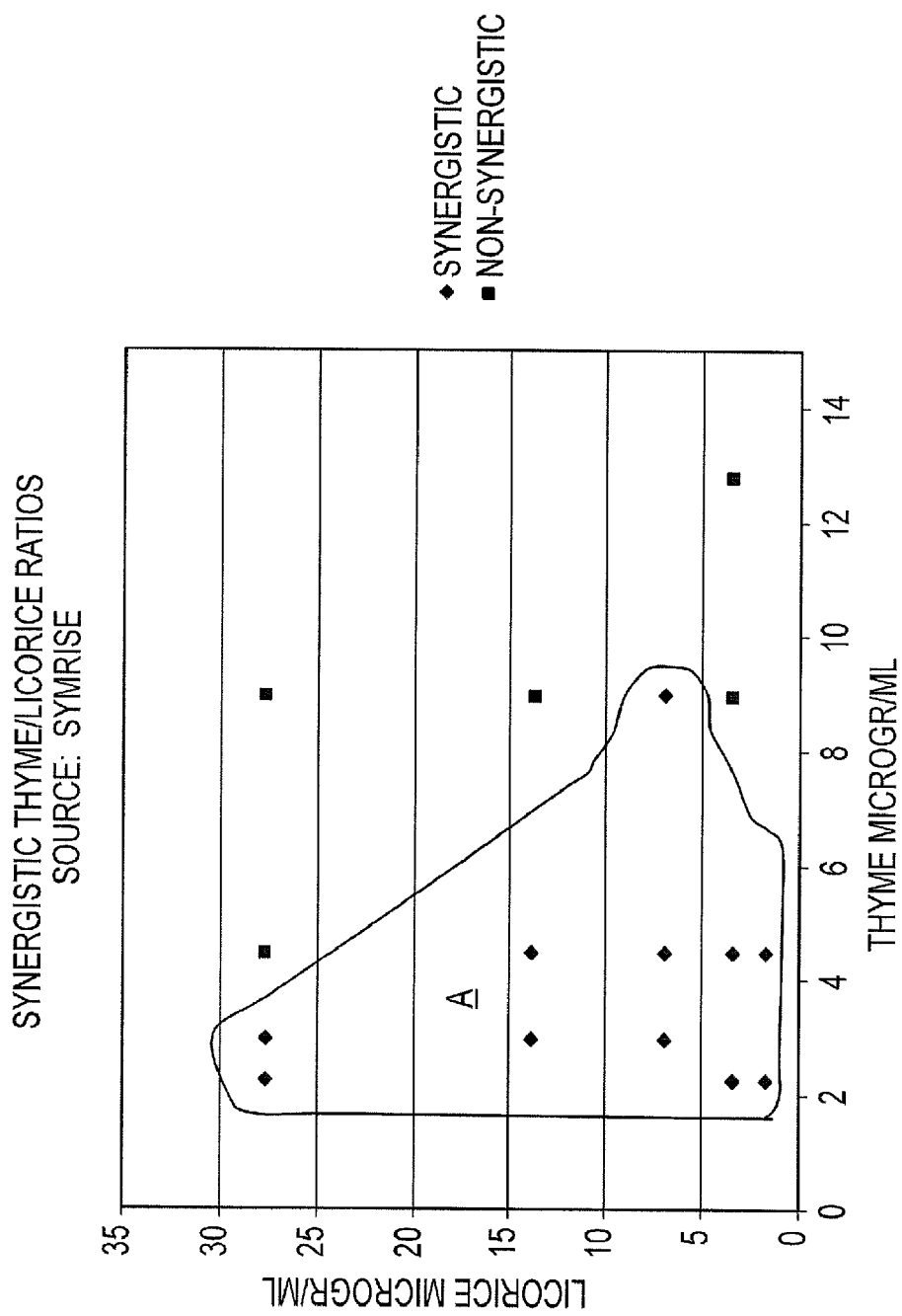

SYNERGISTIC ANTIOXIDANT COMBINATIONS OF HERB EXTRACTS AND METHODS RELATING THERETO

CROSS-REFERENCE TO RELATED APPLICATIONS

This application is a divisional of U.S. application Ser. No. 12/342,483, filed Dec. 23, 2008.

FIELD OF THE INVENTION

The present invention relates to combinations of herb extracts which provide synergistic antioxidant effects when used in personal care products including body washes, lotions, liquid hand soaps, sunscreens, shampoos, and the like. The invention also relates to the methods for preparing skin care preparations incorporating such combinations of herb extracts, as well as the methods for caring for the skin utilizing such preparations.

BACKGROUND

The use of various antioxidant compositions for counteracting the deleterious effect of free radicals upon cells of the human body is widely studied. Free radicals are implicated in a wide variety of diseases of the human body. Referring particularly to diseases of the skin, the presence of free radicals on the skin results from a number of conditions, including over-production of free radicals within the cell itself, or exposure to external forces such as ultraviolet rays, coupled with an inability of the cell itself to defend against the overproduction. The resulting excess of free radicals is known to be the cause of various skin disabilities, such as wrinkling, lack of elasticity, and generalized aging, and there is a need to fortify and supplement the various antioxidant mechanisms in the body.

Many compositions have been proposed and used in the past for providing the desired antioxidant effect, including Vitamin E (tocopherol), Vitamin A (beta-carotene), Vitamin C (ascorbic acid), Trolox (a Vitamin E analog), and the like. In addition, certain plant extracts have been reported as having antioxidant properties, including extracts from birch *Betula platyphylla*) (JP-A-10-046143) and various plant extracts obtained by extraction, with water or a lower alcohol or an aqueous lower alcohol solution, of plants such as hibiscus, aloe, rhubarb, osei (*polygonati rhizoma*), bearberry leaf, enmeiso (*plectranthi herba*), yobaihi (*nyricae cirtex*), pueraria root, cnidium rhizome, atractylodes lancea rhizome, *mentha* leaf, glycyrrhiza, peony root, *coix* seed, sin'i (magnoliae fibs), cinnamon bark, houttuynia herb, coptis rhizome, moutan bark, gentian, nutgall, *swertia* herb, geranium herb, phellodendron bark, dried ginger, *scutellaria* root, chulling (poly porus), garlic, sage, oregano, rosemary, laurel, celery, thyme, tarragon, nutmeg, mace, clove, Japanese horseradish, savory, basil, red pepper, roasted bean, black tea, green tea, persimmon leaf, coffee, horsetail, henon bamboo, mugwort, *Cynostemma* species, low striped bamboo, matrimony vine, *Cyrtomium* species, and shiitake mushrooms (JP-A6-024937). [See US published patent application Publication No. 2004/0028643].

Personal care products such as body washes, lotions, liquid hand soaps, sunscreens, shampoos, and the like ordinarily contain a variety of additives designed to provide performance enhancing benefits such as moisturizing, fragrance, colorant, anti-inflammatory, and anti-irritant properties, and thus these personal care products provide a convenient vehicle for also applying antioxidants directly to the skin. Botanical extracts are a source for many of the above performance enhancing properties and accordingly are conventionally found as additives to the personal care products. To keep the number of additives within reasonable bounds with respect to any particular skin care product, it would be desirable to use herb extracts that provide not only one or more of the performance enhancing properties but also an antioxidant property, and, more particularly, it would be beneficial to find combinations of herb extracts that provide synergistic antioxidant effects. That is, it would be useful to provide formulations of different herb extracts that would function synergistically to increase the total antioxidant activity of the combined extracts in excess of their individual contributions.

SUMMARY OF THE INVENTION

In accordance with one embodiment, the present invention comprises mixtures of herb extracts which exert synergistic antioxidant effect and comprise the herb licorice and at least one other herb selected from the group consisting of ginger, kudzu, sophora, and thyme.

In accordance with another embodiment, the invention comprises a skin care preparation comprising a base which is medicinally acceptable for dermal application and which contains an antioxidant effective mixture of the herb licorice and at least one other herb selected from the group consisting of ginger, kudzu, sophora, and thyme. The invention also comprises a method for the preparations of such skin care preparation.

In accordance with another embodiment, the invention comprises a method for caring for the skin comprising applying to the skin a composition comprising an admixture of a base and an antioxidant effective mixture of the herb licorice and at least one other herb selected from the group consisting of ginger, kudzu, sophora, and thyme.

BRIEF DESCRIPTION OF THE DRAWINGS

FIG. 2-B is an XY scatter chart depicting the synergistic and non-synergistic results from the use of various concentration ratios of kudzu/licorice extract mixtures, in which the kudzu and licorice are in liquid extract form obtained from Symrise GMBH & Co., KG., Holzminden, Germany.

FIG. 4 is an XY scatter chart depicting the synergistic and non-synergistic results from the use of various concentration ratios of thyme/licorice extract mixtures.

DETAILED DESCRIPTION OF THE INVENTION

Figure 1:
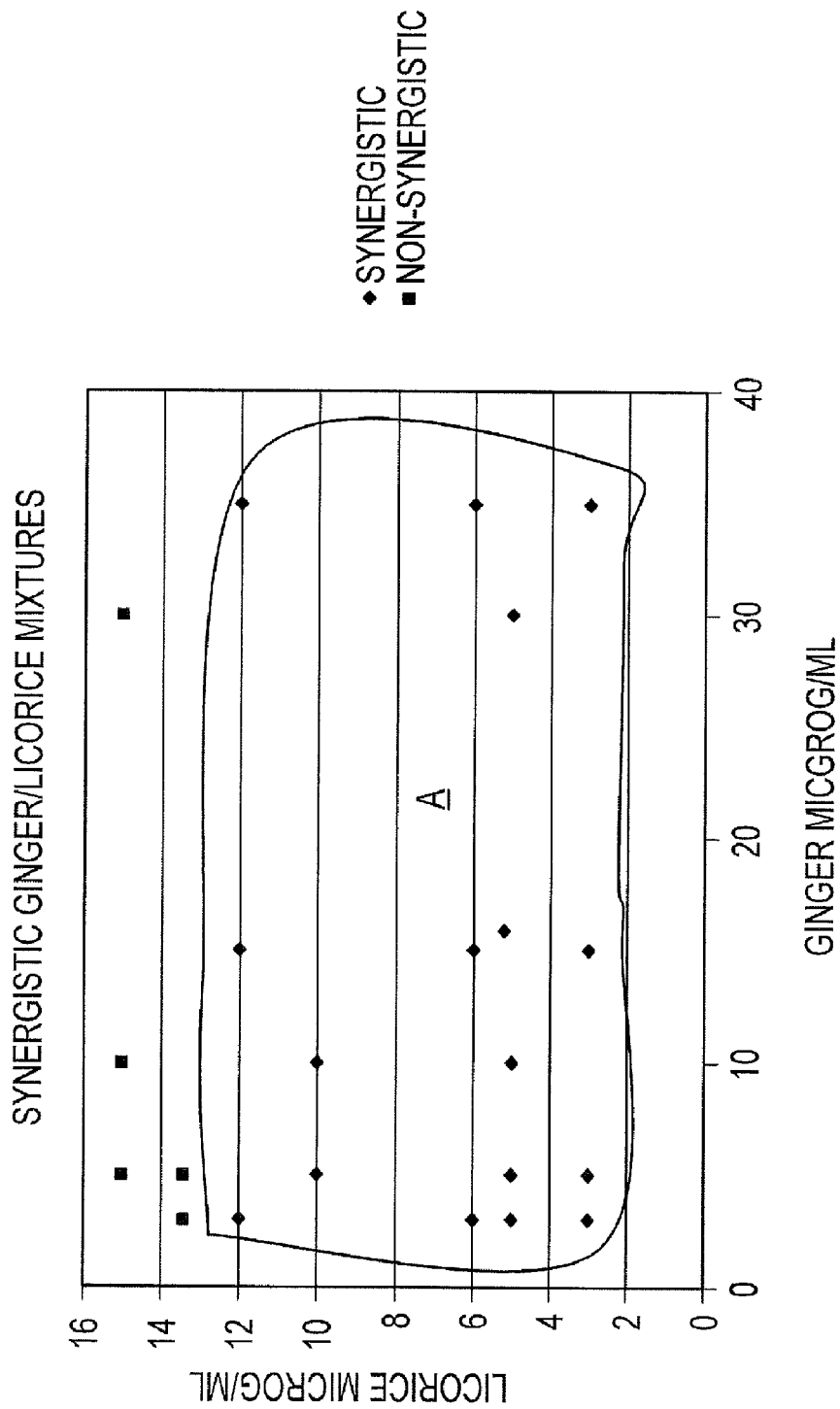
FIG. 1 is an XY scatter chart depicting the synergistic and non-synergistic results from the use of various concentration ratios of ginger/licorice extract mixtures.

This detailed description of various exemplary embodiments of the invention makes reference to exemplary compositions and methods. While these embodiments are described in sufficient detail to enable those skilled in the art to practice the invention, it should be understood that other embodiments may also be realized, and that logical and processing changes may be made without departing from the spirit and scope of the invention. Thus, the detailed description herein is present for the purposes of illustration only and not of limitation.

In the development of the present invention, it was discovered that certain mixtures of extracts of the herb licorice with extracts of other herbs such as ginger, kudzu, sophora, and thyme provide a synergistic antioxidant effect when prepared within certain ranges of concentration ratios. The detailed description of this discovery with respect to each herb mixture (i.e., licorice/ginger, licorice/kudzu, licorice/sophora, and licorice/thyme) will be taken up separately in the sections to follow:

Mixtures of Licorice and Ginger

Licorice is an herb extract obtained from the root of the *Glycyrrhiza glabra* plant, which is indigenous to many sub-tropical climes, including China, Greece, Spain, Turkey, and Iraq. It is mentioned throughout history not only as a candy and food ingredient but also as a natural remedy for a wide range of ailments, including use for anti-inflammatory effect. The licorice extracts used in the present study were obtained from two different sources. The first was a powder extract ordered through Nankai University in China from Shaanxi Hua Teng Biology Project Co. Ltd. The second was a liquid extract obtained on the market from Symrise GMBH & Co., KG., Holzminden, Germany, under the name Actipone® Licorice Root. In the present specification and claims, the extract will be referred to either as "licorice" or as "licorice (powder)" or as "licorice (liquid)", as may be applicable.

Ginger is an herb extract obtained from the rhizome of the perennial plant *Zingiber officinale*, which is indigenous to a number of Asian and Eurasian areas, including China, India, Indonesia, etc. It is mentioned throughout history not only as a candy and food ingredient but also as a natural remedy for a wide range of ailments, including use for anti-inflammatory effect. The ginger extracts used in the present study were obtained from two different sources. The first was a powder extract ordered through Nankai University in China from Sha anxi Hua Teng Biology Project Co. Ltd. The second was a liquid extract obtained on the market from Symrise GMBH & Co., KG., Holzminden, Germany under the name Actipone® Ginger. In the present specification and claims, the extract will be referred to either as "ginger" or as "ginger (powder)" or as "ginger (liquid)", as may be applicable.

In the development of the present invention, the measurement of antioxidant activity was made using the oxygen radical absorbance capacity (ORAC) assay described in the publication by Huang, D.; Ou, B.; Hampshe-Woodill, M.; Flanagan, J. A.; and Prior, R. I., entitled "High-throughput assay of oxygen radical absorbance capacity (ORAC) using a multichannel liquid handling system coupled with a microplate fluorescence reader in 96-well format", 2002 *J. Agric. Food Chem.*, 50, 4437-4444. In these measurements, for each herb extract, the fluorescence decay curves of $Na_2Fl$ induced by AAPH in the presence of Trolox standards was evaluated. The ORAC measurement was performed at 30° C. on a Synergy™ HT multi-detection microplate reader (Bio-Tek Instruments, Inc., Winooski, Vt.) with an excitation wavelength of 485±20 nm and emission wavelength of 530±20 nm. The plate reader was controlled by software KC4 3.4.

In these measurements, an $8.0 \times 10^{-5}$ mM fresh $Na_2Fl$ solution was made daily by diluting the stock solution in 75 mM phosphate buffer (pH 7.4). AAPH (0.414 g) was completely dissolved in 10 ml of 75 mM phosphate buffer (pH 7.4) to a final concentration of 150 mM and was kept in an ice bath. Trolox standard was prepared as follows: 0.0125 g of Trolox was dissolved in 10 ml MeOH solution to give a 0.5M stock solution. The stock solution was diluted with the same phosphate buffer to 50, 25, 12.5 and 6.25 µM, i.e. 12.5, 6.25, 3.13, and 1.56 µg/ml working solutions. These samples were used in each test as control. In each test, samples were freshly prepared by dissolving into 75 mM phosphate buffer (pH 7.4) to make stock solution and then diluting, and the phosphate buffer solution was tested as blank.

In the course of the work leading to the present invention, mixtures of licorice and ginger in a number of varying concentration ratios were tested for antioxidant effectiveness using the ORAC assay method. The fluorescence decay curves of $Na_2Fl$ induced by AAPH in the presence of Trolox standards for each herb extract and the combination of herb extracts were plotted after each test. Their area under the curve (A.U.C.) was calculated. The net A.U.C. was calculated as $A.U.C._{sample} - A.U.C._{blank}$. The net A.U.C. from the combination of herb extracts and the sum of net A.U.C. from each herb extract were listed in table and also plotted in diagram. The results of such testing for a first group of mixtures, using licorice (powder) and ginger (powder) obtained from China are set forth in the following Table 1-A:

TABLE 1-A

Licorice (Powder) and Ginger (Powder)

| Ginger Conc. µg/ml | Licorice Conc. µg/ml | Net A.U.C. | Sum of each herb | Net − Sum | (Net − Sum)/ Sum*100 % |
|---|---|---|---|---|---|
| 10 | 5 | 14.98 | 12.66 | 2.32 | 18.33 |
| 30 | 5 | 28.74 | 25.3 | 3.44 | 13.60 |
| 5 | 10 | 17.68 | 17.32 | 0.36 | 2.08 |
| 5 | 15 | 22.54 | 22.6 | −0.06 | −0.27 |
| 10 | 15 | 25.67 | 26.22 | −0.55 | −2.10 |
| 30 | 15 | 36.18 | 38.86 | −2.68 | −6.90 |
| 15.88 | 5.18 | 17.59 | 15.71 | 1.88 | 11.97 |
| 5 | | 3.25 | | | |
| 10 | | 6.87 | | | |
| 30 | | 19.51 | | | |
| | 5 | 5.79 | | | |
| | 10 | 14.07 | | | |
| | 15 | 19.35 | | | |
| Blank | | 9.52 | | | |

It will be noted that, in the above Table 1-A, a positive percentage number in the (Net-Sum)/Sum*100 column indicates that the mixtures possesses synergistic effect, while a negative percentage number indicates non-synergistic effect.

A second group of licorice/ginger mixtures, but with concentration ratios differing from the first, was submitted to the same ORAC testing, with the results being shown in the following Table 1-B:

TABLE 1-B

Licorice (Powder) and Ginger (Powder)

| Ginger Conc. µg/ml | Licorice Conc. µg/ml | A.U.C | Net AU.C. | Sum of each herb | Net − Sum | (Net − Sum)/ Sum*100* % |
|---|---|---|---|---|---|---|
| 3 | 0 | 6.79 | 1.21 | | | |
| 15 | 0 | 11.78 | 6.2 | | | |
| 35 | 0 | 18.88 | 13.3 | | | |
| 0 | 3 | 8.13 | 2.55 | | | |
| 0 | 6 | 10.56 | 4.98 | | | |
| 0 | 12 | 15.69 | 10.11 | | | |
| 3 | 3 | 10.42 | 4.84 | 3.76 | 1.08 | 28.72 |
| 15 | 3 | 15.41 | 9.83 | 8.75 | 1.08 | 12.34 |
| 35 | 3 | 23.29 | 17.71 | 15.85 | 1.86 | 11.74 |
| 3 | 6 | 12.45 | 6.87 | 6.19 | 0.68 | 10.99 |
| 15 | 6 | 17.38 | 11.8 | 11.18 | 0.62 | 5.55 |

TABLE 1-B-continued

Licorice (Powder) and Ginger (Powder)

| Ginger Conc. µg/ml | Licorice Conc. µg/ml | A.U.C | Net AU.C. | Sum of each herb | Net − Sum | (Net − Sum)/ Sum*100 % |
|---|---|---|---|---|---|---|
| 35 | 6 | 24.47 | 18.89 | 18.28 | 0.61 | 3.34 |
| 3 | 12 | 17.9 | 12.32 | 11.32 | 1 | 8.83 |
| 15 | 12 | 22.89 | 17.31 | 16.31 | 1 | 6.13 |
| 35 | 12 | 31.58 | 26 | 23.41 | 2.59 | 11.06 |
| Blank | | 5.58 | | | | |

It will be noted that, in the above Table 1-B, all numbers in the (Net−Sum)/Sum*100 column are positive numbers, indicating that all concentration ratios provided synergism.

A third group of licorice/ginger mixtures, but with concentration ratios differing from the first two, was submitted to the same ORAC testing, with the results being shown in the following Table 1-C:

TABLE 1-C

Licorice (Powder) and Ginger (Powder)

| Ginger Conc. µg/ml | Licorice Conc. µg/ml | A.U.C | Net A.U.C. | Sum of each herb | Net − Sum | (Net − Sum)/ Sum*100 % |
|---|---|---|---|---|---|---|
| 3 | 0 | 6.25 | 0.8 | | | |
| 5 | 0 | 7.1 | 1.65 | | | |
| 10 | 0 | 9.23 | 3.78 | | | |
| 35 | 0 | 19.59 | 14.14 | | | |
| 0 | 3 | 7.41 | 1.96 | | | |
| 0 | 5 | 8.92 | 3.47 | | | |
| 0 | 10 | 12.46 | 7.01 | | | |
| 0 | 13.42 | 17.85 | 12.4 | | | |
| 3 | 3 | 9.39 | 3.94 | 2.76 | 1.18 | 42.75 |
| 5 | 3 | 10.33 | 4.88 | 3.61 | 1.27 | 35.18 |
| 35 | 3 | 23.29 | 17.84 | 16.1 | 1.74 | 10.81 |
| 3 | 5 | 10.98 | 5.53 | 4.27 | 1.26 | 29.51 |
| 5 | 5 | 13.05 | 7.6 | 5.12 | 2.48 | 48.44 |
| 10 | 5 | 14.05 | 8.6 | 7.25 | 1.35 | 18.62 |
| 5 | 10 | 15.79 | 10.34 | 8.66 | 1.68 | 19.40 |
| 10 | 10 | 17.85 | 12.4 | 10.79 | 1.61 | 14.92 |
| 3 | 13.42 | 17.36 | 11.91 | 13.2 | −1.29 | −9.77 |
| 5 | 13.42 | 17.19 | 11.74 | 14.05 | −2.31 | −16.44 |
| blank | | 5.45 | | | | |

It will be noted that, in the above Table 1-C, a positive percentage number in the (Net-Sum)/Sum*100 column indicates that the mixtures possesses synergistic effect, while a negative percentage number indicates non-synergistic effect.

To summarize the synergistic and non-synergistic findings in the above studies, the synergistic ratios are tabulated below in Table 1-D, and the non-synergistic ratios are set out below in Table 1-E:

TABLE 1-D

Synergistic Licorice/Ginger Concentration ratios

| Ginger µg/ml | Licorice µg/ml |
|---|---|
| 10 | 5 |
| 30 | 5 |
| 5 | 10 |
| 15.88 | 5.18 |
| 3 | 3 |
| 15 | 3 |
| 35 | 3 |
| 3 | 6 |
| 15 | 6 |

TABLE 1-D-continued

Synergistic Licorice/Ginger Concentration ratios

| Ginger µg/ml | Licorice µg/ml |
|---|---|
| 35 | 6 |
| 3 | 12 |
| 15 | 12 |
| 35 | 12 |
| 5 | 3 |
| 3 | 5 |
| 5 | 5 |
| 10 | 10 |

TABLE 1-E

Non-synergistic Licorice/Ginger Concentration ratios

| Ginger µg/ml | Licorice µg/ml |
|---|---|
| 5 | 15 |
| 30 | 15 |
| 10 | 15 |
| 3 | 13.42 |
| 5 | 13.42 |

The data of Tables 1-D and 1-E have been incorporated in an XY scatter chart which is presented in this application as FIG. 1. It will be noted that the concentration ratios found to be synergistic are located within the area marked A on the chart.

To summarize all of the foregoing, in the embodiment of the invention involving mixtures of licorice and ginger, the concentration ratios which have been found to be synergistic are within the range of 3.0 µg/ml $\leq C_{Ginger} \leq$ 35.0 µg/ml, 3.0 µg/ml $\leq C_{Licorice} \leq$ 12.0 µg/ml.

Mixtures of Licorice and Kudzu

In the embodiment involving mixtures of licorice and kudzu, the licorice is the herb extract obtained from the root of the *Glycyrrhiza glabra* plant, which is described in more detail in the previous section. Kudzu is an herb extract obtained from the plant *Pueraria lobata*, which is native to China and Japan but has been transplanted in many other countries of the world, including the United States. It is described as having numerous medicinal uses, particularly in traditional Chinese medicine. The kudzu extracts used in the present study were obtained from two different sources. The first was a powder extract ordered through Nankai University in China from Sha anxi Hua Teng Biology Project Co. Ltd. The second was a liquid extract obtained on the market from Symrise GMBH & Co., KG., Holzminden, Germany under the name Actipone® Pueraria Root. In the present specification and claims, the extract will be referred to either as "kudzu" or as "kudzu (powder)" or as "kudzu (liquid)", as may be applicable.

In the development of the licorice/kudzu embodiment of the present invention, the measurement of antioxidant activity was made using the oxygen radical absorbance capacity (ORAC) assay, which is described in detail in the preceding section relating to the licorice/ginger embodiment.

In the course of the work leading to the present invention, mixtures of licorice and kudzu in a number of varying concentration ratios were tested for antioxidant effectiveness using the ORAC assay method to obtain net A.U.C. values, and the results of such testing for a first group of mixtures, using licorice (powder) and kudzu (powder) obtained from China. are set forth in the following Table 2-A:

TABLE 2-A

Licorice (Powder) and Kudzu (Powder)

| Kudzu Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 1.03 | 4.8 | 14.66 | 9.51 | 7.88 | 1.63 | 20.69 |
| 2.06 | 4.8 | 19.31 | 14.16 | 12.23 | 1.93 | 15.78 |
| 3.09 | 4.8 | 23.42 | 18.27 | 16.36 | 1.91 | 11.67 |
| 1.03 | 9.6 | 18.79 | 13.64 | 11.58 | 2.06 | 17.79 |
| 2.06 | 9.6 | 23.15 | 18 | 15.93 | 2.07 | 12.99 |
| 3.09 | 9.6 | 26.22 | 21.07 | 20.06 | 1.01 | 5.03 |
| 1.03 | 0 | 9.34 | 4.19 | | | |
| 2.06 | 0 | 13.69 | 8.54 | | | |
| 3.09 | 0 | 17.82 | 12.67 | | | |
| 0 | 4.8 | 8.84 | 3.69 | | | |
| 0 | 9.6 | 12.54 | 7.39 | | | |
| Blank | | 5.15 | | | | |

It will be noted that, in the above Table 2-A, all numbers in the (Net−Sum)/Sum*100 column are positive numbers, indicating that all concentration ratios provided synergism A second group of powder licorice/kudzu mixtures, but with concentration ratios differing from the first, was submitted to the same ORAC testing, with the results being shown in the following Table 2-B:

TABLE 2-B

Licorice (Powder) and Kudzu (Powder)

| Kudzu Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 3.05 | 3 | 18.37 | 13.26 | 13.4 | −0.14 | −1.04 |
| 5.08 | 3 | 28.7 | 23.59 | 20.11 | 3.48 | 17.30 |
| 8.13 | 3 | 37.24 | 32.13 | 28.64 | 3.49 | 12.19 |
| 3.05 | 10 | 25.81 | 20.7 | 20.36 | 0.34 | 1.67 |
| 5.08 | 10 | 31.45 | 26.34 | 27.07 | −0.73 | −2.70 |
| 8.13 | 10 | 39.47 | 34.36 | 35.6 | −1.24 | −3.48 |
| 3.05 | 15 | 27.76 | 22.65 | 23.68 | −1.03 | −4.35 |
| 5.08 | 15 | 33.36 | 28.25 | 30.39 | −2.14 | −7.04 |
| 8.13 | 15 | 41.18 | 36.07 | 38.92 | −2.85 | −7.32 |
| 3.05 | 0 | 16.65 | 11.54 | | | |
| 5.08 | 0 | 23.36 | 18.25 | | | |
| 8.13 | 0 | 31.89 | 26.78 | | | |
| 0 | 3 | 6.97 | 1.86 | | | |
| 0 | 10 | 13.93 | 8.82 | | | |
| 0 | 15 | 17.25 | 12.14 | | | |
| Blank | | 5.11 | | | | |

It will be noted that, in the above Table 2-B, a positive percentage number in the (Net−Sum)/Sum*100 column indicates that the mixtures possesses synergistic effect, while a negative percentage number indicates non-synergistic effect.

To summarize the synergistic and non-synergistic findings in the above two studies relating to mixtures of powdered licorice and kudzu, the synergistic ratios are tabulated below in Table 2-C, and the non-synergistic ratios are set out below in Table 2-D:

TABLE 2-C

Synergistic Licorice/Kudzu Concentration ratios (Powdered Extracts from China)

| Kudzu µg/ml | Licorice µg/ml |
|---|---|
| 1.03 | 4.8 |
| 2.06 | 4.8 |
| 3.09 | 4.8 |
| 1.03 | 9.6 |
| 2.06 | 9.6 |
| 3.09 | 9.6 |
| 5.08 | 3 |
| 8.13 | 3 |
| 3.05 | 10 |

TABLE 2-D

Non-synergistic Licorice/Kudzu Concentration ratios (Powdered Extracts from China)

| Kudzu µg/ml | Licorice µg/ml |
|---|---|
| 3.05 | 3 |
| 5.08 | 10 |
| 8.13 | 10 |
| 3.05 | 15 |
| 5.08 | 15 |
| 8.13 | 15 |

Figure 2A:
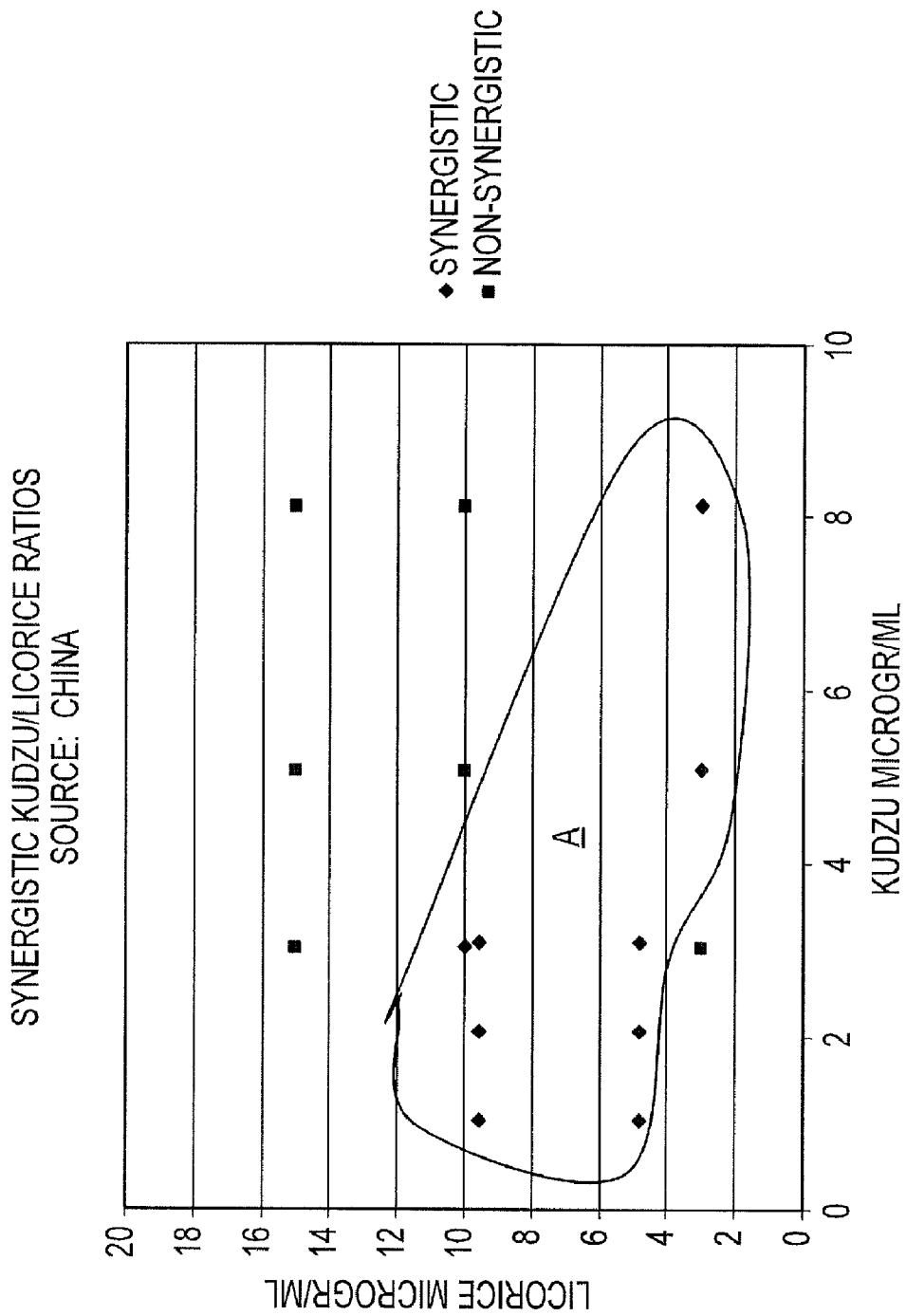
FIG. 2-A is an XY scatter chart depicting the synergistic and non-synergistic results from the use of various concentration ratios of kudzu/licorice extract mixtures, in which the kudzu and licorice are in powder form, obtained from China.

The data of Tables 2-C and 2-D have been incorporated in an XY scatter chart which is presented in this application as FIG. 2-A, relating to powdered kudzu and licorice extracts from China. It will be noted that the concentration ratios found to be synergistic are located within the area marked A on the chart.

To summarize the above data for the embodiment of the invention involving mixtures of powdered kudzu and licorice extracts from China, the concentration ratios which have been found to be synergistic are within the range of $1.0\ \mu g/ml \leq C_{Kudzu} \leq 8.0\ \mu g/ml$, $3.0\ \mu g/ml \leq C_{Licorice} \leq 10.0\ \mu g/ml$.

In addition to the above two groups, third and fourth groups of licorice/kudzu mixtures, but with the herbal extracts in liquid form (from Symrise), were submitted to the same ORAC testing. The results for the third group are shown in the following Table 2-E:

TABLE 2-E

Licorice (Liquid) and Kudzu (Liquid)

| Kudzu Conc. µg/ml | Licorice Conc. µg/ml | A.U.C | Net A.U.C. | Sum of each herb | Net − Sum | (Net − Sum)/ Sum*100 % |
|---|---|---|---|---|---|---|
| 3.56 | 6.92 | 21.97 | 16.72 | 14.8 | 1.92 | 12.97 |
| 4.75 | 6.92 | 25.54 | 20.29 | 18.17 | 2.12 | 11.67 |
| 7.12 | 6.92 | 32.21 | 26.96 | 24.57 | 2.39 | 9.73 |
| 3.56 | 13.84 | 26.26 | 21.01 | 19.12 | 1.89 | 9.88 |
| 4.75 | 13.84 | 29.33 | 24.08 | 22.49 | 1.59 | 7.07 |
| 7.12 | 13.84 | 34.96 | 29.71 | 28.89 | 0.82 | 2.84 |
| 3.56 | 0 | 15.8 | 10.55 | | | |
| 4.75 | 0 | 19.17 | 13.92 | | | |
| 7.12 | 0 | 25.57 | 20.32 | | | |
| 0 | 6.92 | 9.5 | 4.25 | | | |
| 0 | 13.84 | 13.82 | 8.57 | | | |
| blank | | 5.25 | | | | |

It will be noted that, in the above Table 2-E, all numbers in the (Net−Sum)/Sum*100 column are positive numbers, indicating that all concentration ratios provided synergism.

The results for the fourth group of licorice/kudzu mixtures, with the herbal extracts in liquid form (from Symrise), are shown in the following Table 2-F:

TABLE 2-F

Licorice (Liquid) and Kudzu (Liquid)

| Kudzu Conc. µg/ml | Licorice Conc. µg/ml | A.U.C | Net A.U.C. | Sum of each herb | Net − Sum | (Net − Sum)/ Sum*100 % |
|---|---|---|---|---|---|---|
| 1.78 | 18.45 | 19.46 | 13.39 | 15.82 | −2.43 | −15.36 |
| 1.78 | 13.84 | 20.72 | 14.65 | 13.24 | 1.41 | 10.65 |
| 1.78 | 1.73 | 13.11 | 7.04 | 6.24 | 0.8 | 12.82 |
| 3.56 | 27.68 | 34.27 | 28.2 | 26.06 | 2.14 | 8.21 |
| 3.56 | 13.84 | 25.45 | 19.38 | 18.7 | 0.68 | 3.64 |
| 7.12 | 6.92 | 29.94 | 23.87 | 22.58 | 1.29 | 5.71 |
| 7.12 | 3.46 | 28.59 | 22.52 | 20.48 | 2.04 | 9.96 |
| 14.24 | 27.68 | 57.11 | 51.04 | 48.66 | 2.38 | 4.89 |
| 14.24 | 13.84 | 48.31 | 42.24 | 41.3 | 0.94 | 2.28 |
| 14.24 | 1.73 | 41.25 | 35.18 | 34.3 | 0.88 | 2.57 |
| 18.98 | 18.45 | 55.67 | 49.6 | 51.07 | −1.47 | −2.88 |
| 18.98 | 3.46 | 53.44 | 47.37 | 42.43 | 4.94 | 11.64 |
| 18.98 | 1.73 | 50.71 | 44.64 | 41.49 | 3.15 | 7.59 |
| 1.78 | 0 | 11.31 | 5.24 | | | |
| 3.56 | 0 | 16.77 | 10.7 | | | |
| 7.12 | 0 | 24.61 | 18.54 | | | |
| 14.24 | 0 | 39.37 | 33.3 | | | |
| 18.98 | 0 | 46.56 | 40.49 | | | |
| 0 | 1.73 | 7.07 | 1 | | | |
| 0 | 3.46 | 8.01 | 1.94 | | | |
| 0 | 6.92 | 10.11 | 4.04 | | | |
| 0 | 13.84 | 14.07 | 8 | | | |
| 0 | 18.45 | 16.65 | 10.58 | | | |
| 0 | 27.68 | 21.43 | 15.36 | | | |
| Blank | | 6.07 | | | | |

It will be noted that, in the above Table 2-F, a positive percentage number in the (Net−Sum)/Sum*100 column indicates that the mixtures possesses synergistic effect, while a negative percentage number indicates non-synergistic effect.

To summarize the synergistic and non-synergistic findings in the third and fourth groups relating to mixtures of liquid licorice and kudzu, the synergistic ratios are tabulated below in Table 2-G, and the non-synergistic ratios are set out below in Table 2-H:

TABLE 2-G

Synergistic Licorice/Kudzu Concentration ratios (Liquid Extracts from Symrise)

| Kudzu µg/ml | Licorice µg/ml |
|---|---|
| 3.56 | 6.92 |
| 4.75 | 6.92 |
| 7.12 | 6.92 |
| 3.56 | 13.84 |
| 4.75 | 13.84 |
| 7.12 | 13.84 |
| 1.78 | 13.84 |
| 1.78 | 1.73 |
| 3.56 | 27.68 |
| 3.56 | 13.84 |
| 7.12 | 6.92 |
| 7.12 | 3.46 |
| 14.24 | 27.68 |
| 14.24 | 13.84 |
| 14.24 | 1.73 |
| 18.98 | 3.46 |
| 18.98 | 1.73 |

TABLE 2-H

Non-synergistic Licorice/Kudzu Concentration ratios (Liquid Extracts from Symrise)

| Kudzu µg/ml | Licorice µg/ml |
|---|---|
| 1.78 | 18.45 |
| 18.98 | 18.45 |

The data of Tables 2-G and 2-H have been incorporated in an XY scatter chart which is presented in this application as FIG. 2-B, relating to liquid kudzu and licorice extracts from Symrise. It will be noted that the concentration ratios found to be synergistic are located within the area marked A on the chart.

To summarize the above data for the embodiment of the invention involving mixtures of liquid kudzu and licorice extracts from Symrise, the concentration ratios which have been found to be synergistic are within the range of 1.5 µg/ml$\leq C_{Kudzu} \leq$19.0 µg/ml, 1.5 µg/ml$\leq C_{Licorice} \leq$28.0 µg/ml.

Mixtures of Licorice and Sophora Flower

In the embodiment involving mixtures of licorice and sophora flower, the licorice is the herb extract obtained from the root of the *Glycyrrhiza glabra* plant, which is described in more detail in previous sections. Sophora flower is the dried flower of the Japanese pagoda tree (*Sophora japonica*), which is native to Japan, China, Korea and other Eastern Asia countries It is described as having numerous medicinal uses, particularly in traditional Chinese medicine, including use as an anti-inflammatory agent. The sophora flower extracts used in the present study were obtained from Symrise GMBH & Co., KG., Holzminden, Germany under the name Actipone® Sophora Flower. In the present specification and claims, the extract will be referred to either as "sophora" or as "sophora flower."

In the course of the work leading to the present invention, mixtures of licorice and sophora in a number of varying concentration ratios were tested for antioxidant effectiveness using the ORAC assay method to obtain net A.U.C. values, and the results of such testing for a first group of mixtures, using licorice (liquid) and sophora (liquid) obtained from Symrise are set forth in the following Table 3-A:

TABLE 3-A

Licorice (Liquid) and Sophora (Liquid)

| Sophora Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 6.69 | 6.92 | 18.1 | 12.29 | 10.53 | 1.76 | 16.71 |
| 8.92 | 6.92 | 21.41 | 15.6 | 12.79 | 2.81 | 21.97 |
| 13.38 | 6.92 | 25.69 | 19.88 | 17.16 | 2.72 | 15.85 |
| 6.69 | 13.84 | 22.77 | 16.96 | 14.35 | 2.61 | 18.19 |
| 8.92 | 13.84 | 24.5 | 18.69 | 16.61 | 2.08 | 12.52 |
| 13.38 | 13.84 | 29.29 | 23.48 | 20.98 | 2.5 | 11.92 |
| 6.69 | 0 | 12.42 | 6.61 | | | |
| 8.92 | 0 | 14.68 | 8.87 | | | |
| 13.38 | 0 | 19.05 | 13.24 | | | |
| 0 | 6.92 | 9.73 | 3.92 | | | |
| 0 | 13.84 | 13.55 | 7.74 | | | |
| Blank | | 5.81 | | | | |

It will be noted that, in the above Table 3-A, all numbers in the (Net−Sum)/Sum*100 column are positive numbers, indicating that all concentration ratios provided synergism.

A second group of licorice/sophora mixtures, but with concentration ratios differing from the first, was submitted to the same ORAC testing, with the results being shown in the following Table 3-B:

TABLE 3-B

Licorice (Liquid) and Sophora (Liquid)

| Sophora Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 1.67 | 0 | 7.78 | 2.08 | | | |
| 3.34 | 0 | 8.46 | 2.76 | | | |
| 6.69 | 0 | 10.58 | 4.88 | | | |
| 13.38 | 0 | 17.65 | 11.95 | | | |
| 26.75 | 0 | 29.6 | 23.9 | | | |
| 0 | 1.73 | 6.62 | 0.92 | | | |
| 0 | 3.46 | 7.42 | 1.72 | | | |
| 0 | 6.92 | 9.59 | 3.89 | | | |
| 0 | 13.84 | 13.43 | 7.73 | | | |
| 0 | 27.68 | 20.86 | 15.16 | | | |
| 1.67 | 27.68 | 25.57 | 19.87 | 17.24 | 2.63 | 15.26 |
| 1.67 | 6.92 | 12 | 6.3 | 5.97 | 0.33 | 5.53 |
| 1.67 | 1.73 | 8.48 | 2.78 | 3 | −0.22 | −7.33 |
| 3.34 | 27.68 | 26.95 | 21.25 | 17.92 | 3.33 | 18.58 |
| 3.34 | 6.92 | 13.46 | 7.76 | 6.65 | 1.11 | 16.69 |
| 3.34 | 3.46 | 11.18 | 5.48 | 4.48 | 1 | 22.32 |
| 6.69 | 13.84 | 20.85 | 15.15 | 12.61 | 2.54 | 20.14 |
| 6.69 | 3.46 | 14.44 | 8.74 | 6.6 | 2.14 | 32.42 |
| 6.69 | 1.73 | 13.22 | 7.52 | 5.8 | 1.72 | 29.66 |
| 13.38 | 27.68 | 35.62 | 29.92 | 27.11 | 2.81 | 10.37 |
| 13.38 | 6.92 | 21.65 | 15.95 | 15.84 | 0.11 | 0.69 |
| 26.75 | 13.84 | 45.33 | 39.63 | 31.63 | 8 | 25.29 |
| 26.75 | 1.73 | 30.62 | 24.92 | 24.82 | 0.1 | 0.40 |
| Blank | | 5.7 | | | | |

It will be noted that, in the above Table 3-B, a positive percentage number in the (Net−Sum)/Sum*100 column indicates that the mixtures possesses synergistic effect, while a negative percentage number indicates non-synergistic effect.

A third group of licorice/sophora mixtures, but with concentration ratios differing from the first two, was submitted to the same ORAC testing, with the results being shown in the following Table 3-C:

TABLE 3-C

Licorice (Liquid) and Sophora (Liquid)

| Sophora Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 0 | 27.68 | 24.43 | 18.92 | | | |
| 0 | 39.54 | 32.97 | 27.46 | | | |
| 0 | 55.35 | 45.57 | 40.06 | | | |
| 1.67 | 0 | 6.64 | 1.13 | | | |
| 6.69 | 0 | 11.21 | 5.7 | | | |
| 26.75 | 0 | 29.03 | 23.52 | | | |
| 1.67 | 27.68 | 25.16 | 19.65 | 20.05 | −0.4 | −2.00 |
| 1.67 | 39.54 | 33.2 | 27.69 | 28.59 | −0.9 | −3.15 |
| 1.67 | 55.35 | 46.56 | 41.05 | 41.19 | −0.14 | −0.34 |
| 6.69 | 39.54 | 38.05 | 32.54 | 33.16 | −0.62 | −1.87 |
| 6.69 | 55.35 | 50.3 | 44.79 | 45.76 | −0.97 | −2.12 |
| 26.75 | 27.68 | 48.65 | 43.14 | 42.44 | 0.7 | 1.65 |
| Black | | 5.51 | | | | |

It will be noted that, in the above Table 3-C, a positive percentage number in the (Net−Sum)/Sum*100 column indicates that the mixtures possesses synergistic effect, while a negative percentage number indicates non-synergistic effect.

To summarize the synergistic and non-synergistic findings in the above three studies, the synergistic ratios are tabulated below in Table 3-D, and the non-synergistic ratios are set out below in Table 3-E:

TABLE 3-D

Synergistic Licorice/Sophora Concentration ratios

| Sophora µg/ml | Licorice µg/ml |
|---|---|
| 6.69 | 6.92 |
| 8.92 | 6.92 |
| 13.38 | 6.92 |
| 6.69 | 13.84 |
| 8.92 | 13.84 |
| 13.38 | 13.84 |
| 1.67 | 27.68 |
| 1.67 | 6.92 |
| 3.34 | 27.68 |
| 3.34 | 6.92 |
| 3.34 | 3.46 |
| 6.69 | 3.46 |
| 6.69 | 1.73 |
| 13.38 | 27.68 |
| 26.75 | 13.84 |
| 26.75 | 1.73 |
| 26.75 | 27.68 |

TABLE 3-E

Non-synergistic Licorice/Sophora Concentration ratios

| Sophora µg/ml | Licorice µg/ml |
|---|---|
| 1.67 | 1.73 |
| 1.67 | 27.68 |
| 1.67 | 39.54 |
| 1.67 | 55.35 |
| 6.69 | 39.54 |
| 6.69 | 55.35 |

Figure 3:
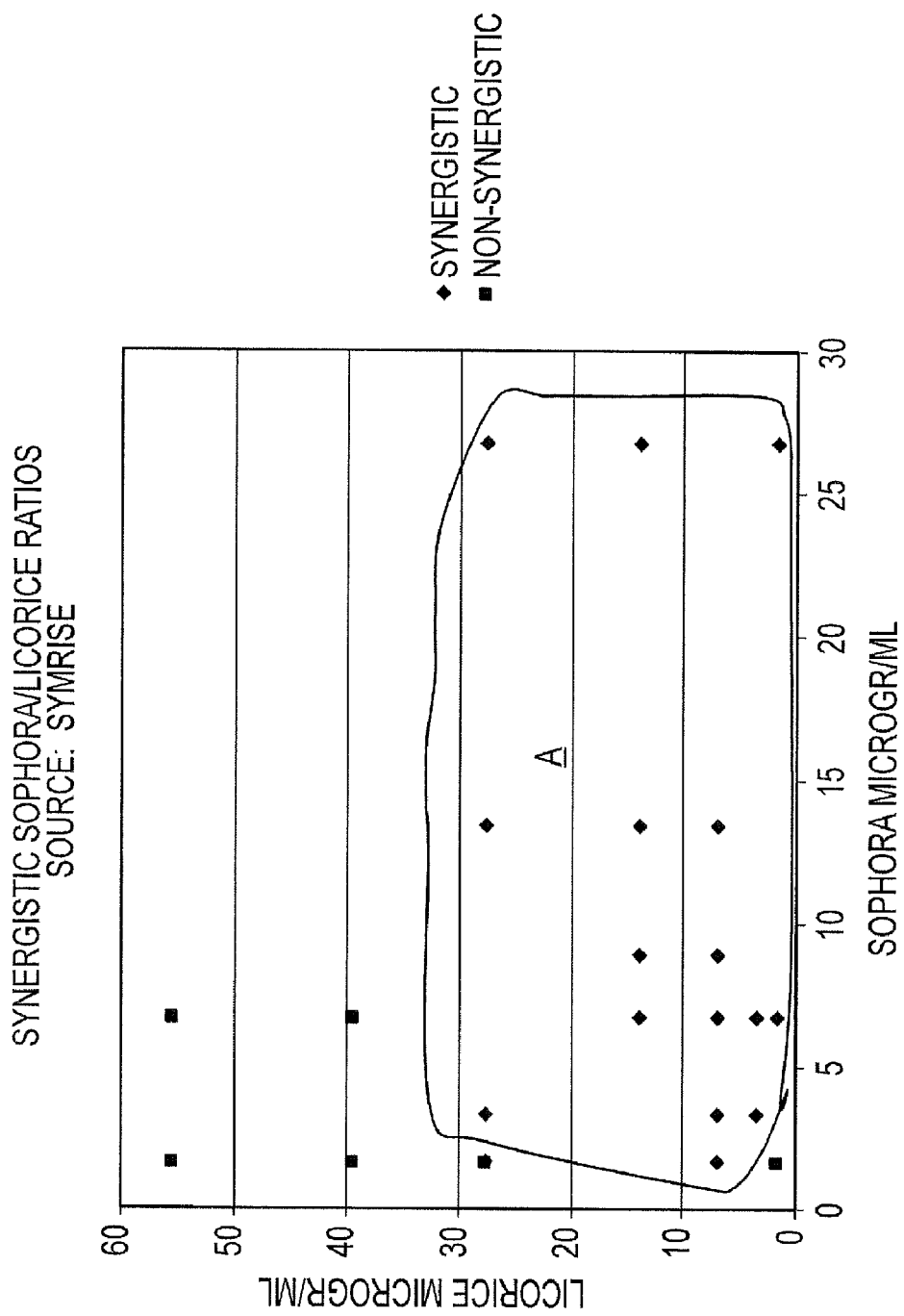
FIG. 3 is an XY scatter chart depicting the synergistic and non-synergistic results from the use of various concentration ratios of sophora/licorice extract mixtures.

The data of Tables 3-D and 3-E have been incorporated in an XY scatter chart which is presented in this application as FIG. 3. It will be noted that the concentration ratios found to be synergistic are located within the area marked A on the chart.

To summarize all of the foregoing, in the embodiment of the invention involving mixtures of licorice and sophora, the concentration ratios which have been found to be synergistic are within the range of 1.5 µg/ml≦$C_{Sophora}$≦27.0 µg/ml, 1.5 µg/ml≦$C_{Licorice}$≦28.0 µg/ml.

Mixtures of Licorice and Thyme

In the embodiment involving mixtures of licorice and thyme, the licorice is the herb extract obtained from the root of the *Glycyrrhiza glabra* plant, which is described in more detail in previous sections. Thyme is a well-known herb, obtained from the leaves of the Mediterranian perennial plant, *Thymus vulgaris*. It is described in the literature as having numerous culinary and medicinal uses, including use as an antiseptic. The thyme extracts used in the present study were obtained from Symrise GMBH & Co., KG., Holzminden, Germany. In the present specification and claims, the extract will be referred to either as "thyme" or as "thyme (liquid)."

In the course of the work leading to the present invention, mixtures of licorice and thyme in a number of varying concentration ratios were tested for antioxidant effectiveness using the ORAC assay method to obtain net A.U.C. values, and the results of such testing for a first group of mixtures, using licorice (liquid) and thyme (liquid) obtained from Symrise are set forth in the following Table 4-A:

TABLE 4-A

Licorice (Liquid) and Thyme (Liquid)

| Thyme Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 2.98 | 6.92 | 19.1 | 13.06 | 12.67 | 0.39 | 3.08 |
| 4.48 | 6.92 | 23.43 | 17.39 | 16.34 | 1.05 | 6.43 |
| 8.95 | 6.92 | 33.54 | 27.5 | 26.38 | 1.12 | 4.25 |
| 2.98 | 13.84 | 23.15 | 17.11 | 16.87 | 0.24 | 1.42 |
| 4.48 | 13.84 | 26.8 | 20.76 | 20.54 | 0.22 | 1.07 |
| 8.95 | 13.84 | 36.47 | 30.43 | 30.58 | −0.15 | −0.49 |
| 2.98 | 27.68 | 30.56 | 24.52 | 24.44 | 0.08 | 0.33 |
| 4.48 | 27.68 | 34.14 | 28.1 | 28.11 | −0.01 | −0.04 |
| 8.95 | 27.68 | 43.52 | 37.48 | 38.15 | −0.67 | −1.76 |
| 2.98 | 0 | 14.72 | 8.68 | | | |
| 4.48 | 0 | 18.39 | 12.35 | | | |
| 8.95 | 0 | 28.43 | 22.39 | | | |
| 0 | 6.92 | 10.03 | 3.99 | | | |
| 0 | 13.84 | 14.23 | 8.19 | | | |
| 0 | 27.68 | 21.8 | 15.76 | | | |
| blank | | 6.04 | | | | |

It will be noted that, in the above Table 4-A, a positive percentage number in the (Net−Sum)/Sum*100 column indicates that the mixtures possesses synergistic effect, while a negative percentage number indicates non-synergistic effect.

A second group of licorice/thyme mixtures, but with concentration ratios differing from the first, was submitted to the same ORAC testing, with the results being shown in the following Table 4-B:

TABLE 4-B

Licorice (Liquid) and Thyme (Liquid)

| Thyme Conc. µg/ml | Licorice Conc. µg/ml | A.U.C | Net A.U.C. | Sum of each herb | Net − Sum | (Net − Sum)/ Sum*100* % |
|---|---|---|---|---|---|---|
| 0 | 1.73 | 6.83 | 1.32 | | | |
| 0 | 3.46 | 8.03 | 2.52 | | | |
| 0 | 27.68 | 24.43 | 18.92 | | | |
| 2.24 | | 12.2 | 6.69 | | | |
| 4.48 | | 18.02 | 12.51 | | | |
| 8.95 | | 28.04 | 22.53 | | | |
| 12.79 | | 35.52 | 30.01 | | | |
| 2.24 | 1.73 | 13.57 | 8.06 | 8.01 | 0.05 | 0.62 |
| 2.24 | 3.46 | 15.64 | 10.13 | 9.21 | 0.92 | 9.99 |
| 2.24 | 27.68 | 34 | 28.49 | 25.61 | 2.88 | 11.25 |
| 4.48 | 1.73 | 19.52 | 14.01 | 13.83 | 0.18 | 1.30 |
| 4.48 | 3.46 | 20.89 | 15.38 | 15.03 | 0.35 | 2.33 |
| 8.95 | 3.46 | 29.88 | 24.37 | 25.05 | −0.68 | −2.71 |
| 12.79 | 3.46 | 37.02 | 31.51 | 41.45 | −9.94 | −23.98 |
| black | | 5.51 | | | | |

It will be noted that, in the above Table 4-B, a positive percentage number in the (Net−Sum)/Sum*100 column indicates that the mixtures possesses synergistic effect, while a negative percentage number indicates non-synergistic effect.

To summarize the synergistic and non-synergistic findings in the above two studies, the synergistic ratios are tabulated below in Table 4-C, and the non-synergistic ratios are set out below in Table 4-D:

TABLE 4-C

Synergistic Licorice/Thyme Concentration ratios

| Thyme µg/ml | Licorice µg/ml |
|---|---|
| 2.98 | 6.92 |
| 4.48 | 6.92 |
| 8.95 | 6.92 |
| 2.98 | 13.84 |
| 4.48 | 13.84 |
| 2.98 | 27.68 |
| 2.24 | 1.73 |
| 2.24 | 3.46 |
| 2.24 | 27.68 |
| 4.48 | 1.73 |
| 4.48 | 3.46 |

TABLE 4-D

Non-synergistic Licorice/Thyme Concentration ratios

| Thyme µg/ml | Licorice µg/ml |
|---|---|
| 8.95 | 13.64 |
| 4.48 | 27.68 |
| 8.95 | 27.68 |
| 8.95 | 3.46 |
| 12.79 | 3.46 |

The data of Tables 4-C and 4-D have been incorporated in an XY scatter chart which is presented in this application as FIG. 4. It will be noted that the concentration ratios found to be synergistic are located within the area marked A on the chart.

To summarize all of the foregoing, in the embodiment of the invention involving mixtures of licorice and thyme, the concentration ratios which have been found to be synergistic are within the range of 2.0 µg/ml $\leq C_{Thyme} \leq$ 9.0 µg/ml, 1.5 µg/ml $\leq C_{Licorice} \leq$ 28.0 µg/ml.

In the practice of the invention, the plant extract combinations mentioned above may be included in any suitable skin care bases medicinally acceptable for dermal application, including various base formulations such as liquids, creams, gels, foams, lotions, body washes, liquid hand soaps, shampoos, antiperspirants, deodorants, and the like. Such base formulations conventionally contain known skin care ingredients, such as found in "CFTA Cosmetic Ingredient Handbook," J. M. Nikitakis, ed., The Cosmetic, Toiletry and Fragrance Association, Inc., Washington, D.C. (1988), incorporated herein by reference. Such ingredients include, but not by way of limitation, numerous enhancing elements, such as alcohols, oleaginous substances, surfactants, preservatives, perfumes, emollients, colorants, humectants, thickening agents, skin care agents, water-soluble polymers, chelating agents, pH adjusting agents, foaming agents, antimicrobial agents, vitamins, and the like.

Examples of the above-mentioned surfactants include, but are not limited to, lauryl sulfates, octyl sulfates, 2-ethylhexyl sulfates, lauramine oxides, decyl sulfates, tridecyl sulfates, cocoates, lauryl sulfosuccinates, lauryl sarcosinates, lauryl ether sulfates (1 and 2 moles ethylene oxide), myristamine oxide, ricinoleates, cetyl sulfates, alkyl glucosides, and similar surfactants.

Examples of the above preservatives include benzoic acid salts, salicylic acid salts, sorbic acid salts, dehydroacetic acid salts, parahydroxybenzoic acid esters, benzalkonium chloride, 2,4,4'-trichloro-2'-hydroxydiphenyl ether, 3,4,4'-trichlorocarbanilide, hinokitiol, resorcinol, and ethanol.

Examples of humectants include glycerin, sodium pyrrolidone carboxylate, and the like. Examples of foam stabilizers include cetyl alcohol, cetearyl alcohol, stearic acid, and the like. Examples of skin care agents include guar gum, hydroxyethylcellulose, hydroxypropylmethylcellulose, polyethylene glycol, hydrolyzed wheat protein, polyoxyethylene stearyl ether, and the like.

The actual formulation of the skin care consumer products incorporating the plant extract combinations of the present invention is through standard methods of manufacturing. All the liquid formulations are easily made in batch mixtures, with addition of water usually first, such that the liquid is above the mixing impeller within the tank. Then the specialty chemicals, such as the surfactants are added, followed by the dyes, preservatives, plant extract combinations, etc. The methods of manufacture are well known.

While numerous exemplary embodiments of the invention have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention set forth in the appended claims and their legal equivalents.

We claim:

1. A composition comprising a mixture of kudzu and licorice extracts which exerts synergistic antioxidant effect and in which the kudzu and licorice are within the concentration range of 1.0 µg/ml$\leq C_{Kudzu} \leq$19.0 µg/ml, 1.5 µg/ml$\leq C_{Licorice} \leq$28.0 µg/ml.

2. The composition of claim 1 in which the kudzu and licorice are in powder form and the licorice and kudzu are within the concentration range of 1.0 µg/ml$\leq C_{Kudzu} \leq$8.0 µg/ml, 3.0 µg/ml$\leq C_{Licorice} \leq$10.0 µg/ml.

3. The composition of claim 1 in which the kudzu and licorice are in liquid form and the licorice and kudzu are within the concentration range of 1.5 µg/ml$\leq C_{Kudzu} \leq$19.0 µg/ml, 1.5 µg/ml$\leq C_{Licorice} \leq$28.0 µg/ml.

4. A skin care preparation comprising a base medicinally acceptable for dermal application having mixed therein the composition of herb extracts as defined in claim 1.

5. A composition of herb extracts which provides synergistic antioxidant effects, comprising a mixture of herb extracts selected from the group consisting of:
   a. a mixture of licorice and powdered kudzu extracts having a concentration falling approximately within the area marked A in the chart shown in FIG. 2-A hereof,
   b. a mixture of licorice and liquid kudzu extracts having a concentration falling approximately within the area marked A in the chart shown in FIG. 2-B hereof.

6. A skin care preparation comprising a base medicinally acceptable for dermal application having mixed therein the composition of herb extracts as defined in claim 5.

* * * * *